United States Patent
Bibi et al.

(10) Patent No.: US 6,691,704 B2
(45) Date of Patent: Feb. 17, 2004

(54) SYSTEM AND METHOD FOR AEROSOL DELIVERY OF A DRUG

(75) Inventors: Noam Bibi, Rehovot (IL); Nimrod Lev, Ganei Yehuda (IL); Eitan Landau, Ramat Gan (IL)

(73) Assignee: Medihale Ltd., Netanya (IL)

( * ) Notice: Subject to any disclaimer, the term of this patent is extended or adjusted under 35 U.S.C. 154(b) by 0 days.

(21) Appl. No.: 10/270,508

(22) Filed: Oct. 16, 2002

(65) Prior Publication Data

US 2003/0034033 A1 Feb. 20, 2003

Related U.S. Application Data (63) Continuation of application No. PCT/IL01/00607, filed on Jul. 1, 2001.

(51) Int. Cl.[7] .............................................. A61M 15/00
(52) U.S. Cl. ................................................. 128/203.21
(58) Field of Search ..................... 128/200.24, 200.11, 128/200.14, 200.21, 200.22, 200.23, 203.21, 203.12, 203.14, 203.19, 203.28, 205.13–205.17, 203.22, 203.24; 604/30, 33, 131, 136, 411, 416, 905; 206/219

(56) References Cited

U.S. PATENT DOCUMENTS

| | | | | |
|---|---|---|---|---|
| 3,921,637 A | * | 11/1975 | Bennie et al. ......... | 128/203.15 |
| 3,971,377 A | | 7/1976 | Damani | |
| 4,046,146 A | | 9/1977 | Rosskamp et al. | |
| 4,240,418 A | | 12/1980 | Rosskamp et al. | |
| 4,318,405 A | | 3/1982 | Sneider | |
| 4,442,941 A | | 4/1984 | Keith | |
| 4,613,063 A | | 9/1986 | Wright | |
| 4,817,800 A | * | 4/1989 | Williams et al. ............. | 206/484 |
| 4,884,565 A | * | 12/1989 | Cocozza ................ | 128/203.01 |
| 4,976,351 A | | 12/1990 | Mangini et al. | |
| 5,046,609 A | | 9/1991 | Mangini et al. | |
| 5,161,524 A | * | 11/1992 | Evans .................... | 128/203.15 |
| 5,318,824 A | | 6/1994 | Itaya et al. | |
| 5,383,850 A | * | 1/1995 | Schwab et al. ............... | 604/58 |
| 5,388,572 A | * | 2/1995 | Mulhauser et al. ..... | 128/203.15 |
| 5,447,151 A | * | 9/1995 | Bruna et al. ............ | 128/203.15 |
| 5,542,411 A | * | 8/1996 | Rex ...................... | 128/203.15 |
| 5,562,918 A | | 10/1996 | Stimpson | |
| 5,595,175 A | * | 1/1997 | Malcher et al. ......... | 128/203.15 |
| 5,634,900 A | * | 6/1997 | Makino et al. ................ | 604/58 |
| 5,694,920 A | | 12/1997 | Abrams et al. | |
| 5,700,998 A | | 12/1997 | Palti | |
| 5,810,004 A | * | 9/1998 | Ohki et al. ............. | 128/203.15 |
| 5,988,163 A | * | 11/1999 | Casper et al. ........... | 128/203.15 |
| 5,989,217 A | * | 11/1999 | Ohki et al. .............. | 604/94.01 |
| 6,045,534 A | | 4/2000 | Jacobsen et al. | |
| 6,089,228 A | * | 7/2000 | Smith et al. ............ | 128/203.15 |
| 6,142,146 A | | 11/2000 | Abrams et al. | |
| 6,183,466 B1 | | 2/2001 | Wong et al. | |
| 6,186,141 B1 | * | 2/2001 | Pike et al. .............. | 128/203.12 |
| 6,248,354 B1 | | 6/2001 | Firestone et al. | |
| 6,280,410 B1 | | 8/2001 | Weston et al. | |
| 6,367,473 B1 | * | 4/2002 | Kafer .................... | 128/203.21 |
| 6,443,152 B1 | * | 9/2002 | Lockhart et al. ........ | 128/203.21 |
| 6,457,471 B1 | | 10/2002 | Bibi | |
| 6,470,884 B2 | * | 10/2002 | Horlin ................... | 128/203.15 |
| 6,475,178 B1 | * | 11/2002 | Krajewski et al. ............. | 604/31 |
| 6,591,832 B1 | * | 7/2003 | DeJonge ................. | 128/203.14 |
| 6,595,210 B2 | * | 7/2003 | Ohki et al. ............. | 128/203.15 |
| 2003/0164169 A1 | * | 9/2003 | Stangl et al. ........... | 128/203.12 |

FOREIGN PATENT DOCUMENTS

EP        0979662       8/1999

* cited by examiner

Primary Examiner—Aaron J. Lewis
Assistant Examiner—Teena Mitchell
(74) Attorney, Agent, or Firm—Mark M. Friedman (57) ABSTRACT

A system and method for aerosol delivery of a drug. The system includes: a disposable cassette containing a dose of the drug. The dose of the drug is supplied within a breakable container. The system further includes a drug release mechanism to break the breakable container and release dose of the drug. Air from the airflow generator flows into the cassette via a first opening and outward via a second opening insuring aerosol delivery of the drug. The method includes supplying a disposable cassette as in the system and operating a drug release mechanism to break the breakable container and release the dose of the drug. The method further includes generating a flow of air top cause aerosol delivery of the drug. An additional method including supplying at least two breakable packets each containing a portion of a pre-measured dose of the drug within a disposable cassette, opening the packets within the cassette and aerosol delivery of the single pre-measured dose of the drug.

17 Claims, 5 Drawing Sheets

SYSTEM AND METHOD FOR AEROSOL DELIVERY OF A DRUG

This application is a Continuation in Part of PCT IL 01/00607 filed on Jul. 01, 2001 which claimed priority from U.S. patent application Ser. No. 09/609,220 filed on Jun. 30, 2000 which issued as U.S. Pat. No. 6,457,471 on Oct. 01, 2002.

FIELD AND BACKGROUND OF THE INVENTION

The present invention relates to a system and method for aerosol delivery of a drug. More particularly the present invention relates to a disposable cassette containing a single pre-measured dose of the drug supplied within at least one breakable container and to methods of use thereof.

Medical disorders of the upper airway are common. Asthma affects approximately 10% of the adult population. Asthmatic patients, together with those suffering from cystic fibrosis, bronchitis, smoking related disorders and infants with difficulty maintaining adequate oral ventilation are probably found in 20–50% of households. Patients with these disorders are generally treated with drugs delivered as an aerosol suspension.

Aerosol delivery of drugs to the airway is typically accomplished by either a stream of air created by a motorized pump, or by use of a pressurized propellant gas (e.g. aerosol canister).

Aerosol delivery devices which include a motorized pump typically require measuring and mixing of components of the aerosol. This provides an opportunity for error during measurement or mixing and may lead to delivery of an incorrect dose of medication. This problem is common to both hospitals and home treatment. In a hospital, a single staff member may treat many patients with different doses of the same drug in the course of a workday. At home a patient, for example one suffering an asthma attack, may be under stress when measuring and mixing components of a mixture.

Devices which rely upon a pressurized propellant gas are typically capable of delivering a pre-measured dose of medication with each actuation (e.g. metered dose inhalers). However, medication packaged in this way is relatively expensive. In addition, patients with poor coordination (e.g. young children, geriatric patients) often have difficulty using these devices. Thus, a device which delivers medicine slowly over the course of a longer period of time is often required.

There is thus a widely recognized need for, and it would be highly advantageous to have, a system and method for aerosol delivery of a drug devoid of the above limitations.

SUMMARY OF THE INVENTION

According to one aspect of the present invention there is provided a dual-purpose medical device for upper airway treatment, the device comprising: (a) a disposable cassette having a first opening, a second opening and an interior volume, the cassette being connectable to an airflow generator by means of the first opening; (b) the airflow generator capable of creating a flow of air through the disposable cassette such that: aerosol delivery of a drug residing in the internal volume of the cassette may be accomplished.

According to another aspect of the present invention there is provided a method for aerosol delivery of a drug, the method comprising the steps of: (a) connecting an airflow generator to a disposable cassette via a first opening of the cassette, the cassette comprising the first opening, a second opening and an interior volume; and (b) causing air to flow into the internal volume of the cassette via the first opening and outward from the internal volume via the second opening towards an airway of a patient such that the aerosol delivery of a drug residing in the internal volume of the cassette is accomplished.

According to further features in preferred embodiments of the invention described below, the device further comprises (c) a re-usable holder for the cassette.

According to still further features in the described preferred embodiments the cassette further comprises: (i) at least one partition dividing the interior volume into at least two chambers; and (ii) an openable region in each of the at least one partition.

According to still further features in the described preferred embodiments the device further comprises a mechanism for opening the openable region.

According to still further features in the described preferred embodiments the method comprises the additional step of: (c) placing the cassette within a re-usable holder.

According to still further features in the described preferred embodiments the method comprises the additional step of (c) providing within the cassette: (i) at least one partition dividing the interior volume into at least two chambers; and (ii) an openable region in each of the at least one partition wherein at least one of the chambers contains at least one component of the drug.

According to still further features in the described preferred embodiments the method comprises the additional step of providing perforations surrounding a portion of the openable region in each of the at least one partition such that opening thereof is facilitated by the perforations.

According to still further features in the described preferred embodiments the method comprises the additional step of opening the openable region by means of mechanism for opening the openable region.

According to still further features in the described preferred embodiments the method comprises the additional step of aerosolizing the drug to form a plurality of micro-droplets by means of an aerosol jet connected to the second opening of the cassette.

According to one aspect of the present invention there is provided a system for aerosol delivery of a drug. The system includes: (a) a disposable cassette containing a single pre-measured dose of the drug within an interior volume of the cassette, the cassette including a first opening, a second opening and the interior volume and being connectable to an airflow generator by means of the first opening; (b) the single pre-measured dose of the drug supplied within at least one breakable container, the at least one breakable container occupying at least a portion of the interior volume of the cassette; (c) a drug release mechanism, the drug release mechanism designed and constructed to break the at least one breakable container and release the single pre-measured dose of the drug. Air from the airflow generator is capable of generating a flow of air into the interior volume of the cassette via the first opening and outward from the interior volume via the second opening towards an airway of a patient such that aerosol delivery of a drug residing in the interior volume of the cassette may be accomplished.

According to another aspect of the present invention there is provided a method of aerosol delivery of a drug, the method includes: (a) supplying a disposable cassette containing a single pre-measured dose of the drug within an interior volume of the cassette, the cassette including a first opening, a second opening and the interior volume and being connectable to an airflow generator by means of the first opening; (b) operating a drug release mechanism designed and constructed to break the at least one breakable container and release the single pre-measured dose of the drug into the interior volume of the cassette; (c) generating a flow of air into the interior volume of the disposable cassette via a first opening thereof and outward from the interior volume via a second opening thereof towards an airway of a patient such that aerosol delivery of the single pre-measured dose of the drug is accomplished. The single pre-measured dose of the drug is contained within at least one breakable container, the at least one breakable container occupying at least a portion of the interior volume of the cassette According to yet another aspect of the present invention there is provided a method of aerosol delivery of a drug. The method includes: (a) supplying at least two breakable packets, each of the packets containing a portion of a single pre-measured dose of the drug, the packets residing within at least a portion of an interior volume of a disposable cassette; (b) opening the packets within the interior volume of the disposable cassette thereby preparing the single pre-measured dose of the drug; and (c) generating a flow of air into the interior volume of the disposable cassette via a first opening thereof and outward from the interior volume via a second opening thereof towards an airway of a patient such that aerosol delivery of the single pre-measured dose of the drug is accomplished. "Preparation" as used herein may refer for example to mixing components of the drug to form an active ingredient or appropriate dilution.

According to further features in preferred embodiments of the invention described below, the further includes a re-usable holder designed and constructed to reversibly engage at least a portion of the cassette. The holder is designed and constructed to facilitate attachment of the cassette to the airflow generator.

According to still further features in the described preferred embodiments the at least one breakable container includes at least two breakable containers.

According to still further features in the described preferred embodiments engagement of the re-usable holder to the cassette serves to operate the drug release mechanism.

According to still further features in the described preferred embodiments the drug release mechanism includes a piston designed and constructed to be linearly displaced along an axis of the interior volume, thereby breaking the at least one breakable container.

According to still further features in the described preferred embodiments the cassette further includes a third opening to facilitate insertion of the piston into the interior volume of the cassette.

According to still further features in the described preferred embodiments the piston further includes at least one protuberance designed and constructed to break the breakable container as the piston is linearly displaced.

According to still further features in the described preferred embodiments at least one opening selected from the group consisting of the first opening and the second opening is located on the piston.

According to still further features in the described preferred embodiments the system further includes an aerosol jet connectable to the second opening of the cassette and capable of delivering the drug as a plurality of micro-droplets.

According to still further features in the described preferred embodiments the method further includes reversibly engaging at least a portion of the disposable cassette by means of a re-usable holder, the holder designed and constructed to facilitate attachment of the cassette to the airflow generator.

According to still further features in the described preferred embodiments the single pre-measured dose of the drug is contained within at least two breakable containers.

According to still further features in the described preferred embodiments the reversibly engaging the re-usable holder to the cassette serves to operate the drug release mechanism.

According to still further features in the described preferred embodiments operating the drug release mechanism includes linearly displacing a piston along an axis of the interior volume, thereby breaking the at least one breakable container.

According to still further features in the described preferred embodiments the method further includes providing an aerosol jet connectable to the second opening of the cassette and capable of delivering the drug as a plurality of micro-droplets.

According to still further features in the described preferred embodiments the method further includes providing a third opening, in the cassette to facilitate insertion of the piston into the interior volume thereof.

The present invention successfully addresses the shortcomings of the presently known configurations by providing a system and method for aerosol delivery of a drug which relies upon a single pre-measured dose of the drug.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a system and method for aerosol delivery of a drug. Specifically, the present invention can be used to deliver a single pre-measured dose of the drug supplied within at least one breakable container.

The principles and operation of a system and method for aerosol delivery of a drug for upper airway treatment and of methods for using the device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the term "drug" refers to any material which is delivered for purposes of therapy. Intended therapy may work by, for example, a physiologic mechanism or a simple physical effect. The term drug therefore specifically includes, but is not limited to, water, saline solutions, vasoconstrictors, antihistamines, steroid compounds, decongestants, aroma-therapy agents, plant extracts, oils, anti-inflammatory compounds and antibiotics as well as any combination thereof. A drug may take many physical forms, including but not limited to, a liquid, a powder, a gel, an emulsion, a gas, and a solid. It will be appreciated that those solids which have a high vapor pressure at room temperature, i.e. those which tend to sublime, are more suited for use as a drug in the context of the present invention than those solids with a low vapor pressure at room temperature.

For purposes of this specification and the accompanying claims, the term "patient" refers to any person or animal using the device of, or practicing a method of, the present invention.

Referring now to drawings 1a, 1b, 2a, and 2b, a narrative description of the component parts of a system 20 for upper airway treatment, and their workings, will be presented. System 20 for aerosol delivery of a drug includes a disposable cassette 22 containing a single pre-measured dose 24 of the drug within an interior volume 30 of cassette 22. Dose 24 may occupy any portion of, or essentially all of, interior volume 30 of cassette 22. Cassette 22 includes a first opening 26, a second opening 28 and interior volume 30. Cassette 22 is further connectable to an airflow generator 36 by means of first opening 26. Connection may be accomplished, for example, by means of mated connectors 32 and 34. Connectors 32 and 34 may be joinable by, for example, by matching threads, a luer lock, or any other reversible connection means. Single pre-measured dose 24 of the drug is supplied within at least one breakable container 40 (optionally one or more additional containers 42) occupying at least a portion of interior volume 30 of cassette 22. System 20 further includes a drug release mechanism 38 designed and constructed to break at least one breakable container 40 and/or 42 and release the single pre-measured dose 24 of the drug. As explained hereinabove, release may include mixing of components to form an active ingredient and/or dilution. Preferably, at least one breakable container 40 includes at least two breakable containers 42. This arrangement allows different components of dose 24 to remain separate until use, insuring maximum activity of the drug at time of delivery.

Air from airflow generator 36 is capable of generating a flow of air into interior volume 30 of cassette 22 via first opening 26 and outward from interior volume 30 via second opening 28 towards an airway of a patient such that aerosol delivery of dose 24 of the drug residing in interior volume 30 of cassette 22 as a plurality of micro-droplets 59 may be accomplished.

Preferably, system 20 further includes a re-usable holder 44 designed and constructed to reversibly engage at least a portion 50 of cassette 22. Holder 44 is designed and constructed to facilitate attachment of cassette 22 to airflow generator 36. Thus, one or both of connectors 32 and 34 may be functionally integrated into holder 44. In one preferred mode of practice, engagement of re-usable holder 44 to cassette 22 serves to operate drug release mechanism 38.

Drug release mechanism 38 may include, for example, a piston 52 designed and constructed to be linearly displaced along an axis 54 of interior volume 30 of cassette 22 thereby breaking at least one breakable container 40 or 42.

According to some preferred embodiments of the invention (see FIGS. 1*a* and 1*b*) cassette 22 further includes a third opening 29 to facilitate insertion of piston 52 into interior volume 30 of cassette 22.

Piston 52 may optionally include at least one protuberance 56 designed and constructed to break breakable containers 40 or 42 as piston 52 is linearly displaced along axis 54. According to various preferred embodiments of the invention, either first opening 26 or second opening 28 may be located on piston 52.

Efficiency of system 20 may be further enhanced by inclusion of an aerosol jet 58 connectable to second opening 28 of cassette 22 and capable of delivering the drug as a plurality of micro-droplets 59.

The present invention is further embodied by a method 80 of aerosol delivery of a drug including supplying 82 a disposable cassette 22 containing 86 single pre-measured dose 24 of the drug within interior volume 30 of cassette 22 as described hereinabove. Method 80 further includes operating 84 a drug release mechanism designed and constructed to break breakable container(s) 40 and/or 42 and release single pre-measured dose 24 of the drug into interior volume 30 of cassette 22. Method 80 further includes generating 88 a flow of air into interior volume 30 of disposable cassette 22 via first opening 26 thereof and outward from the interior volume via second opening 28 thereof as described hereinabove. Dose 24 of the drug is contained 86 within at least one breakable container 40 occupying at least a portion of interior volume 30 of cassette 22. Preferably dose 24 of the drug is supplied 94 contained within at least two breakable containers 42.

Preferably method 80 further includes reversibly engaging 90 at least a portion of disposable cassette 22 by means of a re-usable holder 44 designed and constructed to facilitate attachment of cassette 22 to airflow generator 36. More preferably, reversibly engaging 90 re-usable holder 44 to cassette 22 serves to operate 92 drug release mechanism 38.

Operating 84 drug release mechanism 38 preferably includes linearly displacing 96 piston 52 along axis 54 of interior volume 30, thereby breaking at least one breakable container 40 or 42. Method 80 optionally includes locating 100 either of openings 26 or 28 on piston 52. According to some embodiments of the invention method 80 further includes providing 81 a third opening 29 in cassette 22 to facilitate insertion of piston 52 into interior volume 30. Alternately, or additionally, including 98 a protuberance on piston 52 is a part of method 80.

Optionally, but also preferably, method 80 further includes providing 102 an aerosol jet 58 connectable to second opening 28 of cassette 22 and capable of delivering the drug as a plurality of micro-droplets 59. Aerosol jet 58 may be one of many commercially available devices, for example a microsprayer™ (PennCentury, Inc., Philadelphia, Pa., USA). Aerosol jet 58 may discharge into a spacer, such as an aerosol cloud enhancer and face mask (e.g. one produced by DHD Health Care Corporation, Canastota, N.Y., USA or DEY, Napa, Calif., USA), or to any tube used for endoscopy (e.g. bronchoscope, gastroscope).

Figure 1A:
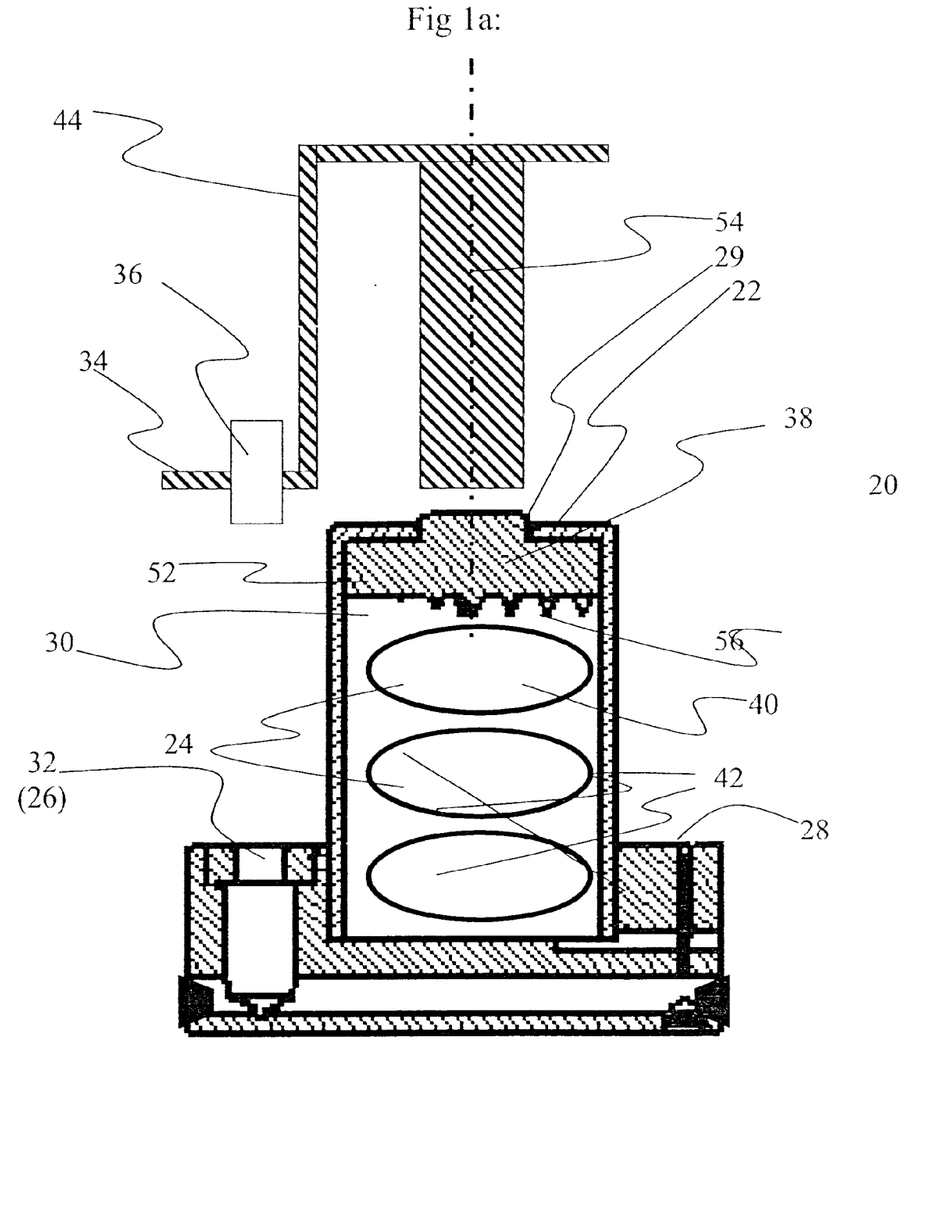
FIGS. 1a and 1b are cross sectional views of a first embodiment of a system according to the present invention demonstrating operation thereof for aerosol delivery of a drug.
Figure 1B:
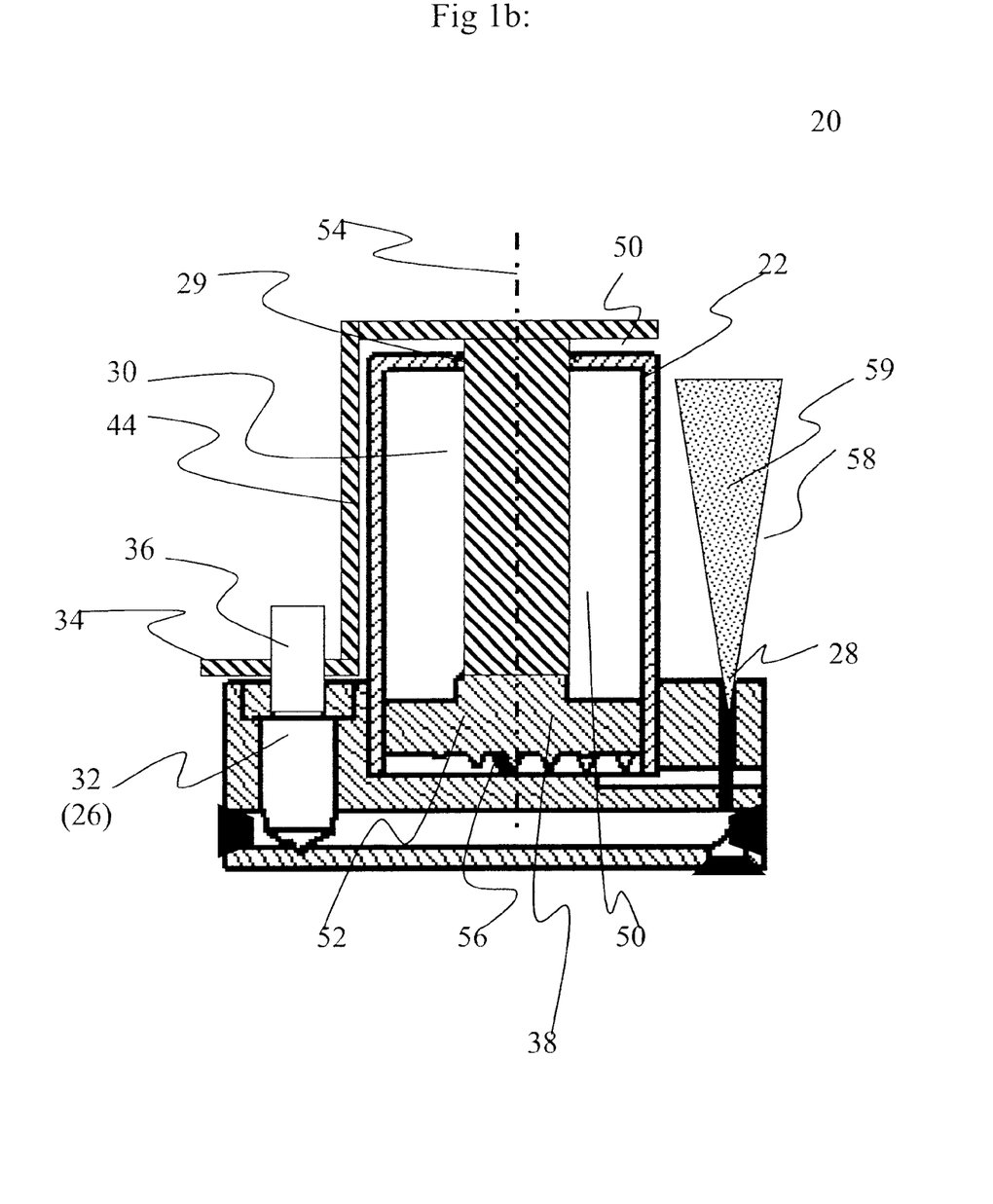
Figure 2A:
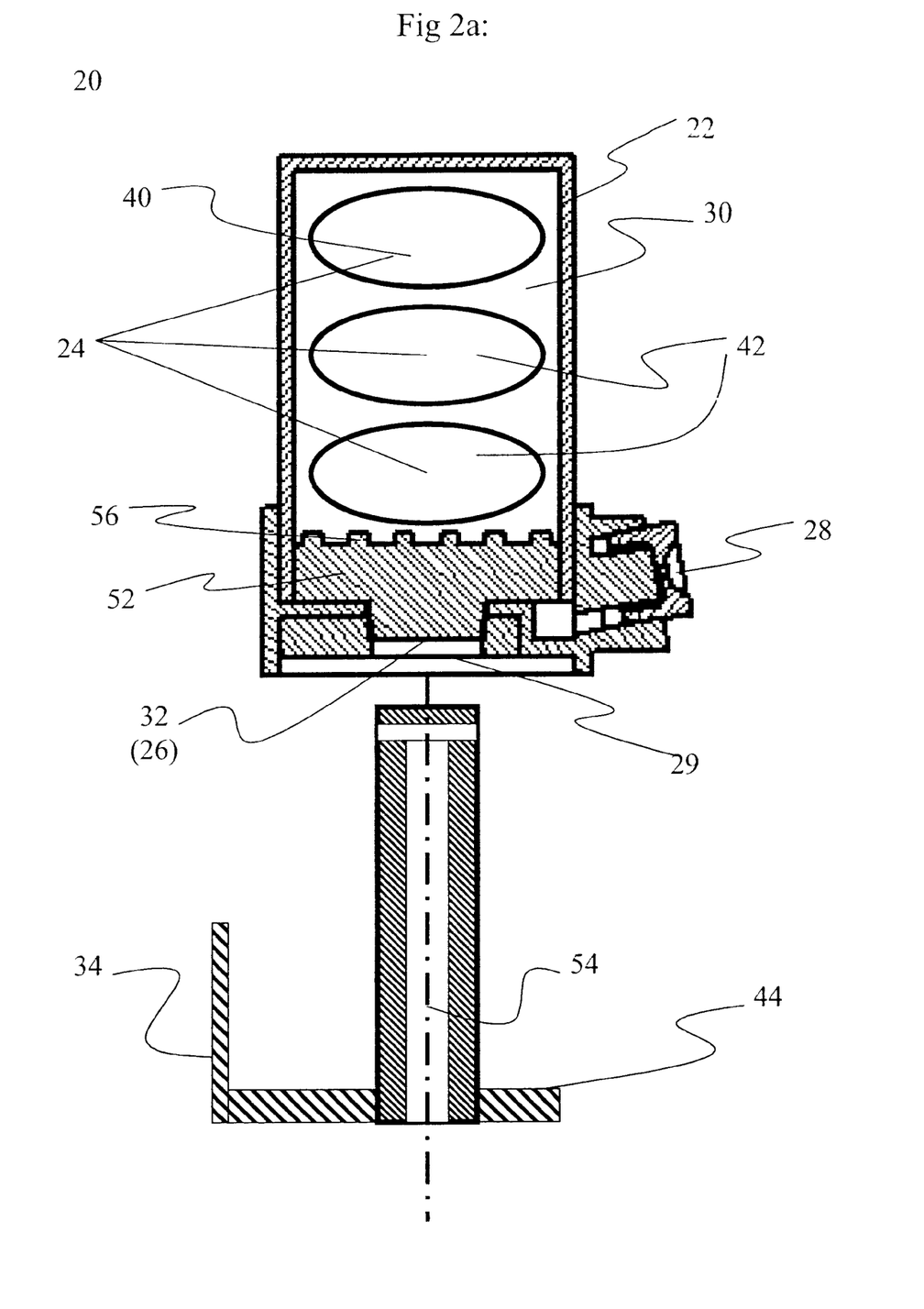
FIGS. 2a and 2b are cross sectional views of an additional embodiment of a system according to the present invention demonstrating operation thereof for aerosol delivery of a drug.
Figure 2B:
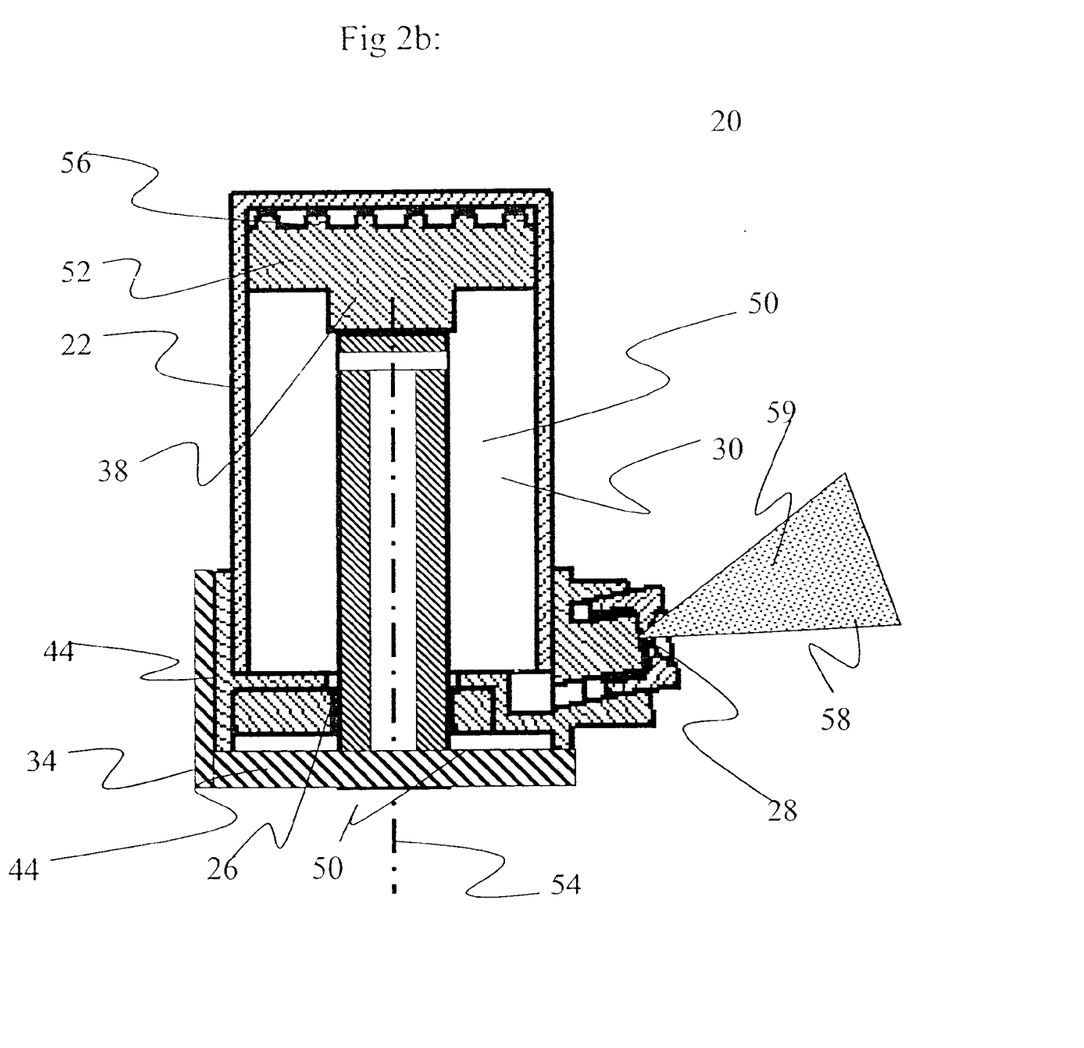
Figure 3:
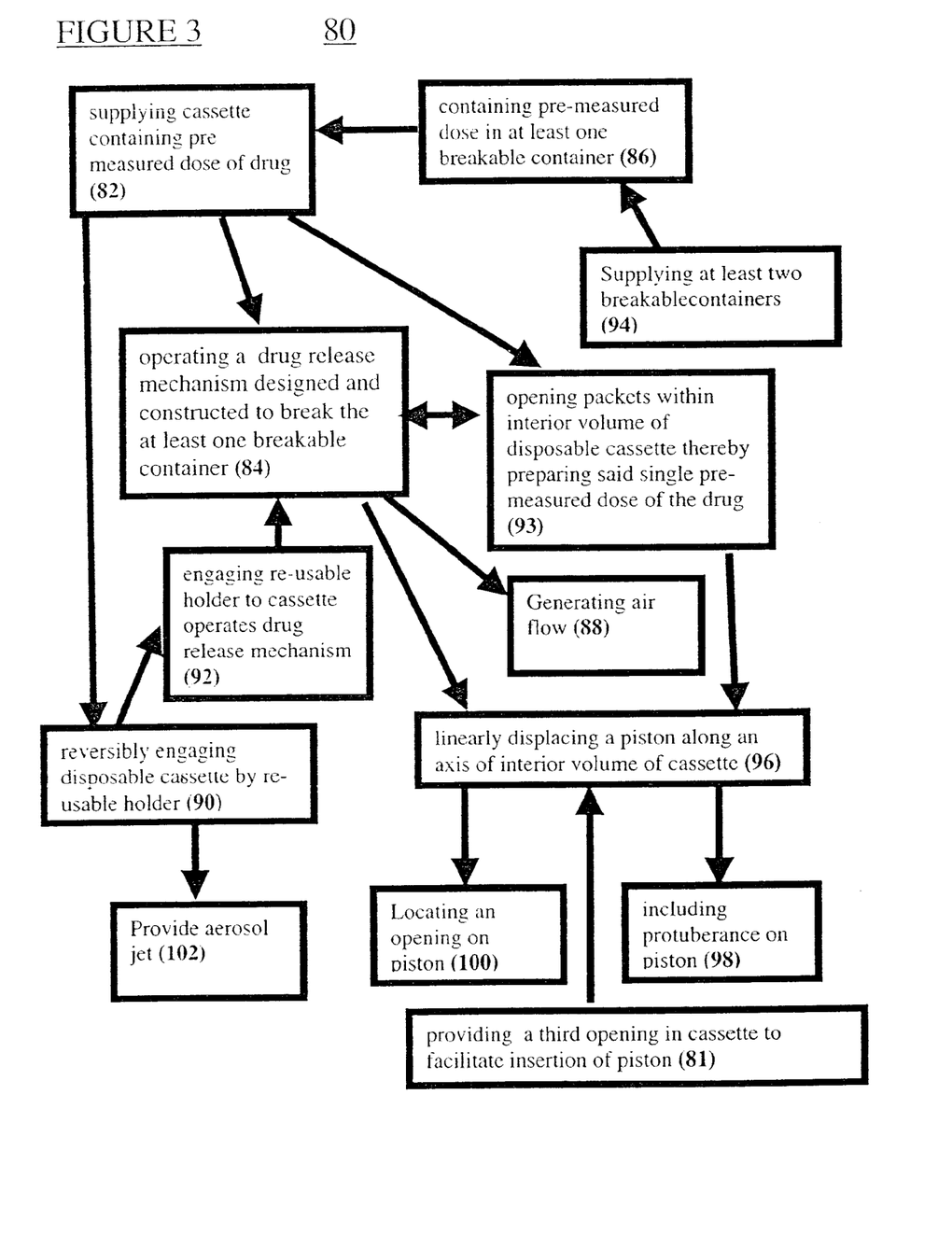
FIG. 3 is a simplified flow diagrams showing steps in methods according to the present invention.

An additional method 80 includes supplying 94 at least two breakable packets or containers 42 each containing a portion of a single pre-measured dose 24 of the drug. Packets reside, or are contained 86 within at least a portion of interior volume 30 of disposable cassette 22. Method 80 further includes opening 93 packets 42 within interior volume 30 of disposable cassette 22 thereby preparing single pre-measured dose 24 of the drug and generating 88 a flow of air into interior volume 30 of disposable cassette 22 as described hereinabove such that aerosol delivery of the single pre-measured dose of the drug is accomplished.

It will be appreciated that re-usable holder 44 for cassette 22 may be supplied either as a separate unit, or constructed as an integral portion of airflow generator 36, or supplied with cassette 22 inside. Holder 44 may have fixed sides and an openable top, or at least one openable side, or both. Openable top and side may be equipped with, for example, hinges in order to facilitate opening of holder 44.

It will be appreciated that cassette 22 includes at least one partition in the form of containers 40 and 42 dividing interior volume 30 into at least two chambers. Each partition 40 and 42 includes therein at least an openable region. Perforations may surround at least a portion of each openable region in partition 40 and 42 such that opening thereof is facilitated by the perforations. A mechanism for opening (e.g. piston 52) openable region 40 and 42 is further provided. Alternately or additionally, increased air pressure in cassette 22 may be used to open the openable region.

The mechanism for opening may include, for example, a moveable piston 52 including a plate capable of translational motion along axis 54 within interior 30 of cassette 22. Translational motion of moveable plate of piston 52 may be achieved, for example, by pressing on a widened end of piston 52 protruding from holder 44, causing openable regions of containers 40 and 42 to be opened (e.g. by breaking perforations). This creates channels of fluid communication between containers 40 and 42 and interior 30 of cassette 22. This fluid communication may facilitate, for example, mixing of components of a drug to be delivered via aerosol as air flows through interior 30.

Alternately, or additionally, mechanism for opening may include at least one piston 52 having a widened end and being moveable against spring tension of springs. Piston 52 moves within hole 26 and an end thereof is capable of contacting openable regions of containers 40 and 42 and opening them, for example by breaking perforations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for aerosol delivery of a drug, the system comprising:

(a) a disposable cassette containing a single pre-measured dose of the drug within an interior volume of said cassette, said cassette including a first opening, a second opening and said interior volume and being connectable to an airflow generator by means of said first opening;

(b) said single pre-measured dose of the drug supplied within at least two breakable containers, said at least two breakable containers occupying at least a portion of said interior volume of said cassette;

(c) a drug release mechanism, said drug release mechanism designed and constructed to break said at least two breakable containers and release said single pre-measured dose of the drug;

wherein air from said airflow generator is capable of generating a flow of air into, said interior volume of said cassette via said first opening and outward from said interior volume via said second opening towards an airway of a patient such that aerosol delivery of a drug residing in said interior volume of said cassette may be accomplished.

2. The system of claim 1, further comprising:

(d) a re-usable holder designed and constructed to reversibly engage at least a portion of said cassette, said holder designed and constructed to facilitate attachment of said cassette, to said airflow generator.

3. The system of claim 2, wherein engagement of said re-usable holder to said cassette serves to operate said drug release mechanism.

4. The system of claim 1, wherein said drug release mechanism includes a piston designed and constructed to be linearly displaced along an axis of said interior volume, thereby breaking said at least two breakable containers.

5. The system of claim 4, wherein said piston further includes at least one protuberance designed and constructed to break said at least two breakable containers as said piston is linearly displaced.

6. The system of claim 4, wherein said cassette further comprises a third opening, said third opening facilitating insertion of said piston into said interior volume.

7. The system of claim 4, wherein at least one opening selected from the group consisting of said first opening and said second opening is located on said piston.

8. The system of claim 1, further comprising an aerosol jet connectable to said second opening of said cassette and capable of delivering said drug as a plurality of microdroplets.

9. A method of aerosol delivery of a drug, the method comprising:

(a) supplying a disposable cassette containing a single pre-measured dose of the drug within an interior volume of said cassette, said cassette including a first opening, a second opening and said interior volume and being connectable to an airflow generator by means of said first opening;

wherein said single pre-measured dose of the drug is contained within at least two breakable containers, said at least two breakable containers occupying at least a portion of said interior volume of said cassette;

(b) operating a drug release mechanism designed and constructed to break said at least two breakable containers and release said single pre-measured dose of the drug into said interior volume of said cassette;

(c) generating a flow of air into said interior volume of said disposable cassette via a first opening thereof and outward from said interior volume via a second opening thereof towards an airway of a patient such that aerosol delivery of said single pre-measured dose of the drug is accomplished.

10. The method of claim 9, further comprising:

(d) reversibly engaging at least a portion of said disposable cassette by means of a re-usable holder, said holder designed and constructed to facilitate attachment of said cassette to said airflow generator.

11. The method of claim 10, wherein said reversibly engaging said re-usable holder to said cassette serves to operate said drug release mechanism.

12. The method of claim 9, wherein said operating said drug release mechanism includes linearly displacing a piston along an axis of said interior volume, thereby breaking said at least two breakable containers.

13. The method of claim 12, further comprising providing a third opening, in said cassette to facilitate insertion of said piston into said interior volume thereof.

14. The method of claim 12, wherein said piston further includes at least one protuberance designed and constructed to break at least two breakable containers as said piston is linearly displaced.

15. The method of claim 12, wherein at least one opening selected from the group consisting of said first opening and said second opening is located on said piston.

16. The method of claim 9, further comprising providing an aerosol jet connectable to said second opening of said cassette and capable of delivering said drug as a plurality of micro-droplets.

17. A method of aerosol delivery of a drug, the method comprising:

(a) supplying at least two breakable packets, each of said packets containing a portion of a single pre-measured dose of the drug, said packets residing within at least a portion of an interior volume of a disposable cassette;

(b) opening said packets within said interior volume of said disposable cassette thereby preparing said single pre-measured dose of the drug; and (c) generating a flow of air into said interior volume of said disposable cassette via a first opening thereof and outward from said interior volume via a second opening thereof towards an airway of a patient such that aerosol delivery of said single pre-measured dose of the drug is accomplished.

* * * * *